United States Patent [19]

Coursaget et al.

[11] Patent Number: 4,464,474
[45] Date of Patent: Aug. 7, 1984

[54] NON-A, NON-B HEPATITIS ASSAY AND VACCINE

[75] Inventors: Pierre L. J. Coursaget, Saint Avertin; Philippe C. Maupas, Rochecorbon, both of France

[73] Assignee: Connaught Laboratories Limited, Willowdale, Canada

[21] Appl. No.: 167,282

[22] Filed: Jul. 9, 1980

[51] Int. Cl.³ .................... G01N 33/54; G01N 33/56; G01N 33/58
[52] U.S. Cl. .................... 436/513; 436/531; 436/804; 436/820
[58] Field of Search .................... 424/1, 12; 23/230 B; 436/513, 331, 804, 820

[56] References Cited

U.S. PATENT DOCUMENTS

| | | | |
|---|---|---|---|
| 3,887,697 | 6/1975 | Vyas et al. | 424/12 |
| 4,012,494 | 3/1977 | Ling | 424/12 X |
| 4,013,411 | 3/1977 | Shupack et al. | 424/12 X |
| 4,100,267 | 7/1978 | Shaw | 424/12 X |
| 4,133,873 | 1/1979 | Noller | 23/230 B |
| 4,157,280 | 6/1979 | Halbert et al. | 23/230 B |
| 4,189,464 | 2/1980 | Blumberg et al. | 424/1 |
| 4,202,665 | 5/1980 | Wenz et al. | 23/230 B |
| 4,234,564 | 11/1980 | McAleer et al. | 424/12 |
| 4,356,164 | 10/1982 | Tabor et al. | 424/1 |

OTHER PUBLICATIONS

Shirachi et al., The Lancet, Oct. 21, 1978, pp. 853–856.
Gocke et al., J. Immunology, vol. 104, Apr. 1970, pp. 1031–1032.
Tabor et al., Gastroenterology, 76:680–684, 1979.
Tabor et al., The Lancet, Mar. 4, 1978, pp. 463–466.
Tabor et al., from *Viral Hepatitis*, ed. Vyas et al., Franklin Institute Press, Philadelphia, 1978, pp. 419–421.

*Primary Examiner*—Christine M. Nucker
*Attorney, Agent, or Firm*—Sim & McBurney

[57] ABSTRACT

A newly discovered particle in the urine and serum of non-A, non-B hepatitis patients has been associated with non-A, non-B hepatitis. The particle resembles a togavirus and is 50–60 nm in diameter with a discrete core of about 40 nm in diameter. The virus loses its infectivity for tissue culture upon heating at 25° C. in aqueous suspension or by exposure to ether. The particle may be cultured in vitro or recovered from body fluids or tissues to make immunoassays and vaccines. The immunoassays may be employed to detect the particle antigens or antibodies thereto in test samples.

8 Claims, No Drawings

NON-A, NON-B HEPATITIS ASSAY AND VACCINE

BACKGROUND OF THE INVENTION

This invention relates to the detection and prevention of infection by a newly discovered etiological agent for non-A, non-B (NANB) hepatitis. In particular it is concerned with making vaccines and conducting immunoassays for this agent or its antibodies.

NANB hepatitis is defined as clinical hepatitis which cannot be attributed to infection by cytomegalovirus, Epstein-Barr virus, or hepatitis A or B.

NANB hepatitis was first identified in transfused individuals. Transmission from man to chimpanzee and serial passages in chimpanzees provided evidence that NANB hepatitis is due to an infectious agent or agents. NANB hepatitis represents up to 90% of post-transfusion hepatitis cases since HBsAg positive blood is no longer used for transfusion. The risk of contracting NANB hepatitis after blood transfusion has been estimated to be close to 10% in the United States. Therefore, it is important to screen the blood of potential donors to detect NANB hepatitis. Further, use of donors vaccinated against NANB hepatitis would serve to reduce the probability of transmitting serum hepatitis.

NANB hepatitis has been found to be associated with a variety of virus-like particles found in serum and tissue extracts. Hollinger et al., in "Proc. Second Symposium on Viral Hepatitis" (San Francisco), p. 699, (1978) report the previous work of others in locations 20-22 nm and 60-80 nm particles associated with NANB hepatitis. Other particles which have been reported to be associated with NANB hepatitis are (a) small spheres and filaments 15-25 nm in diameter, (b) 35-40 nm diameter virions which resemble the hepatitis B DANE particle, (c) a 27 nm viruslike particle identified in lots of antihemophilic factor and liver tissue from chimpanzees infected with antihemophilic factor ("Morbidity and Mortality Weekly Report" 27 (21) [1978]), and (d) a 20-27 nm diameter particle identified in hepatocytes of infected animals (Shimizu et al., "Science" 205: 197-200 [1979]). In addition, antigen-antibody systems not linked to a definitive particle have been identified as associated with NANB hepatitis (Kabiri et al., "Lancet", Aug. 4, 1979, pp. 221-224; Vitvitski et al., "Lancet", Dec. 15, 1979, pp. 1263-1267; Dienstag et al., "Lancet", June 16, 1979, pp. 1265-1267; and Shirachi et al., "Lancet", Oct. 21, 1978, pp. 853-856).

OBJECTS OF THE INVENTION

A principal object of this invention is to locate and isolate from its host environment a virus particle which is an etiological agent for NANB hepatitis.

An additional object is to purify the particle without altering its antigenic characteristics.

A further object is to prepare a vaccine from the particle.

Another object is to elicit or harvest antibodies against the particle for administration as therapeutic gamma globulin or for use in immunoassays for detecting the particle.

A further object is to produce insolubilized particle antigens or antibodies thereto, particularly for use in immunoassays or for purification of the particle antigens or antibodies.

A still further object is to provide labelled, particularly enzyme or radiolabelled, particle antigens or antibodies.

These and other objects of the invention will be apparent from consideration of this specification as a whole.

SUMMARY OF THE INVENTION

The above objects are achieved by:

(1) compositions comprising (a) an antigen of one or more of togavirus strains ATCC VR-2011, VR-2012, VR-2013 or VR-2014, which is substantially free of primate proteins, (b) At least one of the togavirus strains ATCC VR-2011, VR-2012, VR-2013 or VR-2014, which is inactivated or attenuated so as to be biologically non-infectious, (c) primate antibody which is substantially free of other primate proteins and which is capable of binding at least one antigen of togavirus strains ATCC VR-2011, VR-2012, VR-2013 or VR-2014, (d) nonprimate antibody which is capable of binding at least one antigen of one or more togavirus strains ATCC VR-2011, VR-2012, VR-2013 or VR-2014, and (e) any of the foregoing four compositions bound to a water insoluble substance or to a label;

(2) methods for making the compositions supra;

(3) an immunoassay comprising, detecting or determining an antigen of at least one of togavirus strains ATCC VR-2011, VR-2012, VR-2013 or VR-2014;

(4) an immunoassay comprising detecting or determining NANB hepatitis particle core antigen or an antibody thereto;

(5) an immunoassay, comprising detecting or determining IgM capable of binding NANB hepatitis particle antigen;

(6) a method for recovering NANB hepatitis antigens, comprising separating from urine a NANB hepatitis virus antigen;

(7) a method for detecting NANB hepatitis which comprises assaying for a NANB hepatitis particle antigen in urine; and (8) a method for propagating NANB hepatitis virus comprising culturing the virus in a primate diploid cell line.

DETAILED DESCRIPTION OF THE INVENTION

We have located a particle resembling a togavirus in the body fluids of NANB hepatitis patients. The particle ranges from about 50 to 60 nm in diameter and has a core of about 40 nm. It is rendered noninfective for tissue culture by exposure to ether or upon heating at 25° C. in aqueous suspension. The particle was unexpectedly found in urine with greater consistency than in serum. Further, we found that the particle can be cultured in vitro.

Four examples of the particle have been accessioned in the American Type Culture Collection (ATCC) under numbers VR-2011, VR-2012, VR-2013 or VR-2014.

The term "particle" henceforth refers to these ATCC deposits, collectively and individually. These four samples of the particle were discovered by electronmicroscopy in the urine of four patients in the acute state of NANB hepatitis during a hepatitis epidemic in Algeria. The particle was also detected by electronmicroscopy in the urine of five other NANB hepatitis patients out of a total of ten patients whose urines were inspected for the particle. Additionally, three of the five urine samples were infective for tissue culture. Paradoxically, none of the particles could be detected by electronmicroscopy in the sera of ten acute NANB hepatitis patients. Nonetheless, the particle has been detected in the sera of NANB hepatitis-infected patients. Out of eight hemodialysis patients whose serum glutamate-pyruvate transaminose activity (SGPT) was elevated above normal, the serum of one patient taken at the peak of SGPT activity contained the particle as revealed by electronmicroscopy. Finally, the particle has been detected in a sample of commercial blood protein fraction concentrate which had been linked to serum hepatitis infection in recipients of the concentrate.

The particle may be cultured in vitro using a cell line susceptible to infection by the particles, usually human or primate diploid lines, preferably of fetal origin. Examples are the MRC-5 and WI-38 lines. They may be obtained commercially or similar cell lines prepared in the laboratory using conventional techniques.

Any culture medium conventionally used to grow and maintain the susceptible cell line is satisfactory for initially culturing and then sustaining the cells during viral replication. The preferred medium for use with the MRC-5 and WI-38 lines is disclosed by Morgan et al., "Proc. Soc. Biol. Med." 73:1 (1950). It is supplemented with antibiotics and a small proportion, usually about from 5% to 15% by volume, of human or animal serum. If human serum is used it should obviously be free of antibodies to the particles.

The particles are replicated in vitro by culturing the host cells to confluence, inoculating with pathologic sample (preferably urine) having about from $1 \times 10^6$ to $1 \times 10^8$ particles/ml and incubating at about from 30°–40° C. for about from 2 to 7 days while maintaining the culture medium pH at about neutrality. Air is satisfactory for the viral cultivation, i.e., no special atmosphere was needed. The culture medium should be exchanged every 2 days during viral replication. The first subculture will produce about from $1 \times 10^4$ to $1 \times 10^5$ particles/ml. These particles are not infective for further culture and are therefore believed to have become attenuated as a result of replication under the conditions described. As will be described below, such particles may be useful as vaccines.

The particles are recovered from the culture by simply decanting and combining the spent media from the culture container and purified using one or more of the procedures described below. The purified particles are preferably frozen in a medium consisting of 50% of the growth medium without serum and 50% glycerol by volume.

It may be desirable for a variety of reasons to purify the particles present in pathological material such as tissues, urine and blood fractions, or which are obtained through tissue culture. For example, if the particle is to be treated and employed as a vaccine or in an immunoassay, there ordinarily should be as little in the way of extraneous protein contamination as possible. Thus, the particle or its antigens should be substantially free of primate proteins. The term substantially free does not mean that the particle antigen is devoid of proteins present in its natural environment which are noncovalently bound or absorbed thereto, e.g., antibodies. However, the term does mean that all but trace contaminant concentrations of the proteins associated with the particle or particle antigen have been removed, e.g., normal human serum proteins, urinary albumin and cellular proteins.

The particle antigen is defined as a substance containing at least one epitopic site of one of the deposited particles. Thus, a "particle antigen" could be found on a particle which is otherwise immunologically distinct from deposited particles. A "particle antigen" may also be present on a fragment or in solution which is free of any other antigenic sites present on the deposited particles. Particle antibody is defined as an antibody capable of binding a particle antigen as described. It should be noted that the term refers not to the water solubility of the antigen or antibody but rather to their origin or specificity.

The particles may also be reproduced in vivo by injecting particles (usually or preferably $10^9$–$10^{10}$ particles) from pathological material into a chimpanzee not having an antibody titer for the particles, followed by daily inspection of serum and aliquots for the first appearance of the particle. Plasmapheresis can then be used to recover large quantities of contaminated plasma. Alternatively, the animal may be sacrificed and the liver excised and homogenized as a source of particles.

Particle antigens, whether soluble or in the form of intact particles, are first separated from water insoluble contaminants having greater dimensions or different density than the intact particles. Such contaminants may include animal cell debris, e.g., from tissue culture, cellular microorganisms, e.g., bacteria in urine, or chylomicra in sera. This gross separation is generally accomplished by low speed centrifugation or filtration, the parameters of which will obviously vary depending upon the nature and degree of contamination and can be determined by routine experimentation. Either technique may be supplemented by sedimentation with a sucrose density gradient. However, filtration is preferred for large volumes of particle suspension. Ordinarily, filters having an average pore diameter of 0.8 micron are useful in retaining gross contamination and passing the particles.

The particle may be separated from undesired water soluble materials after gross contamination is removed. Where it is desired to only recover intact particles or their water insoluble fragments, e.g., discrete core or envelope fragments, it is convenient to simply remove all water soluble constituents from the sample. This is preferalbly accompanied by replacement of the contaminating solutes with one or more protein stabilizers such as hydroxyl compounds, e.g., sugars, glycerol or carbohydrates, sulfhydryl compounds such as cysteine, and proteins such as serum albumin. Buffers may also be included. The foregoing objectives may be accomplished by ultrafiltering the sample through a membrane having a molecular weight cut-off intermediate the approximately 50 million of the particle and the nearly 1 million of most commonly encountered protein contaminants. The ultrafiltrate is then washed with a buffered solution of the stabilizer, the ultrafilter backwashed with the solution and the washed ultrafiltrate then recovered.

It may be more convenient to precipitate the particles or their large molecular weight fragments using one or more of various well-known flocculating or protein precipitating agents, particularly salting out agents or flocculating polymers. Examples include polyethylene glycol and ammonium sulfate. The precipitating agent may be readily removed from the precipitate by dialysis and the particles resuspended for further purification or use.

The concentration of polyethylene glycol to be used will depend upon whether or not the particles are intact, the electrolyte constituents of the sample, the temperature, the molecular weight of the polyethylene glycol and the degree of contamination by the particles. Polyethylene glycol of average molecular 6000 may be added to serum to a concentration of about from 10 to 15% by weight at a temperature of about from 1° to 5° C. to precipitate the particles. Precipitation from urine may not require as much polethylene glycol as with serum.

The ammonium sulfate concentration to be used is dependent upon the factors noted above for polyethylene glycol, except that the precipitant molecular weight is not a variable. Generally, ammonium sulfate at about from 12 to 18% of saturation is satisfactory to precipitate the particles.

Certain other methods, while ordinarily only useful on a small scale, are well suited for obtaining particles of a high degree of purity. Such high purity particles are useful in immunoassays, especially as immunogens or labelled reagents. Suitable methods include ultracentrifugation, e.g., sedimentation with a sucrose gradient or isopycnic centrifugation with cesium chloride, zone electrophoresis, and chromatography with ion exchange resins, gels or insolubilized specific binding proteins.

Chromatography is the most versatile method since it may be readily scaled up for commercial manufacture of the particles. Gel chromatography systems using cross-linked dextran beads are preferred due to the comparatively low cost. A column of suitable gel can be selected which will permit diffusion of proteins and low molecular weight substances into the void volume of the gel beads, thereby retarding the progress of these contaminants through the column, while allowing the particles to pass through virtually unimpeded. The gel which is selected will thus be a matter of routine experimentation.

Any of the above methods may be combined as desired. For example, gel chromatography of contaminated serum on Biogel A5M and subsequent isopycnic centrifugation in cesium chloride is very effective at removing human serum proteins.

If a large proportion of the particle antigens present in a sample are particle fragments or water soluble protein antigens, then the most expeditious technique for separating them may be affinity chromatography. Antibodies capable of binding the particle antigens are covalently linked or absorbed to an insoluble support using conventional procedures. The insoluble antibody is placed in a column and the sample is passed through. Immunologically-bound antigen is washed with buffer and then released by changing the ionic strength or pH of the wash buffer. Generally, acid pH is effective at releasing the bound antigen. This technique is highly effective in separating closely related proteins from the particle antigens.

The substances which may be removed from urine upon purification of the particles include one or more of urea, bilirubin, uric acid, albumin, mucins, and electrolytes comprising calcium, iron, sodium, potassium, magnesium, chloride, phosphate, ammonia and sulfate.

All of the foregoing materials may also be separated from particle-bearing serum or plasma. In addition, one or more of the following lipids or proteins may also be removed from serum in purifying the particles: Cholesterol; phosphatides, fatty acids, albumin, $\alpha_1$-globulins, $\alpha_2$-globulins, B-globulins, fibrinogen, gamma globulins and lipoprotein members of the $\alpha_1$ and B globulins.

The particles obtained from pathological sources such as serum or urine may be complexed with antibody. Particle antigens free of adherent antibody are desirable for use as reagents for immunoassays. They may be obtained by growing the particle in tissue culture, followed by passing the spent culture through a column of insolubilized staphylococcal Protein A made in known fashion. The Protein A will specifically absorb most residual immune complexes of particle antigen and antibody.

Purified antibody to particle antigen is also useful in immunoassays. The impure anti-serum source may be the sera of patients convalescing from a NANB hepatitis infection or an animal which has been immunized against the particle antigens. The immunized animals may be nonprimates, generally guinea pigs, rabbits, goats or horses, which are not susceptible to hepatitis and thus can be injected with particles which would otherwise be infective and potentially fatal. The antibody-containing gamma globulin fraction may be purified by any conventional protein fractionation procedures previously employed to separate gamma globulin from plasma, e.g., alcohol, polyethylene glycol or ammonium sulfate precipitation.

The degree of antibody purity desired will depend upon the source and intended use. Gamma globulin for therapeutic or prophylactic administration in the treatment or prevention of NANB hepatitis should be of human origin and should be of as high degree of purity as commercially feasible. Usually, this at least entails removing the other undesirable fractions of human plasma, e.g., antihemophilic factor or prothrombin complex, from the donor plasma. On the other hand, it is usually sufficient to employ unfractionated serum from nonprimates in immunoassays, either as insoluble or labelled reagents as will be described below.

Purified particle antigens are further treated for use as vaccines. It is preferred to use as a starting material for preparation of vaccine the particle antigens produced by tissue culture of the infectious virus. The antigens are preferably recovered as intact particles by purifying them as described above. However, it is also possible to prepare a suitable vaccine from particles purified from the serum or urine of acute-phase human patients, or from fragments of the particles from any source, including water soluble antigenic proteins. Such proteins native to the viral envelope are preferred. These proteins may be purified by affinity chromatography, also as described above. It is desirable but not necessary to purify the particle antigens substantially free of human proteins, particularly any adherent gamma globulins in the event a circulatory fluid of an acute NANB hepatitis patient is used as the starting material. However, it is more important that the antigens be free of proteins not of human origin which may be introduced by way of the nutrient medium, cell lines or tissues in which the virus is cultured.

While it is conceivable that noninfectious particle antigen can be isolated free of infective particles without further treatment it is desirable to process the particle antigen-containing suspension to attenuate or inactivate any potentially infective virions. This may be accomplished in a fashion that will not significantly affect the immunogenic or antigen characteristics of the preparation by adding an inactivating agent. Formalin is effective for this purpose. A satisfactory procedure entails adding formalin to the antigen-containing solution or suspension and incubating under conditions which will destroy the infectivity of the composition, usually incubation at about from 25° to 40° C. for about from 4 to 5 days. The formalin is then removed or neutralized, although a bacteriostatically effective amount of formalin, e.g., 10 μg/ml, may be left active. The viral particle count is adjusted to about from $1 \times 10^7$ to $1 \times 10^{11}$ particles by the addition of a physiologically acceptable carrier such as saline or by removal of excess diluent through ultrafiltration, or lyophilization followed by reconstitution with an aqueous solution of the carrier.

Vaccination may be conducted in conventional fashion, for example by subcutaneous administration of 1 ml amounts of the vaccine at biweekly intervals for 14 weeks.

Any of the immunoassay methods heretofore disclosed in the art may be used to determine particle antigens or antibodies. The following disclosure is generally expressed in terms of determining antigens. However, antibodies may be determined using the same methods.

The analytical methods described herein for assaying the particle antigens or antibodies should not be construed as requiring the determination of all of the particle antigens or epitopic sites. Similarly, it is not necessary to assay for all of the antibodies which can bind the population of epitopic sites presented by the particle. The reason for this is that mutations and varieties of viruses are frequently found in nature. Thus, some antibodies originally obtained by immunizing an animal against the particle may not bind, or may bind very weakly to related NANB hepatitis strains. Fortunately, the intact particle described herein is so large that a considerable number of epitopic sites on or within the particle can bind an equal number of discrete, specific antibodies. Thus, changes in one or more of the epitopic sites by mutation or degradation of the particle structure due to environmental stress will not adversely affect an immunoassay using antibodies raised against the entire population of epitopic sites since a proportion of the antibody population will remain capable of binding an equivalent proportion of the antigens. Similarly, antibody produced against even a single antigen common to the particle and the sample antigen can be effectively employed in an assay for either the intact particle or any fragment thereof which contains the antigen. This is the case (a) whether or not the antibody used to detect the antigen was in fact raised by immunization against applicants' deposited particle, against a cross-reacting strain isolated de novo from nature, or against a fragment of said strain or new isolate, and (b) whether or not the antigen used to detect the antibody was derived from the deposited particle, a new isolate of a cross-reacting strain or a fragment of either the deposited particle or new isolate. Cross-reactivity is deemed to exist if an antibody raised against an antigen of the deposited particle can bind with the antigen in question with at least about 40% of the avidity as the antibody will bind the antigen against which it was originally raised.

Particle antigens may be divided into two groups, surface and core antigens. Surface antigens are those which are expressed by the intact particle. These antigens are generally those viral proteins which are exposed to the environment through the lipid-containing envelope. They are the antigens of greatest interest in diagnosis because the intact particle is most likely to be infective and is generally found in early states of the disease.

Incomplete particles may be found or manufactured which consist of the 40 nm diameter core only. Stress which destroys the envelope or incomplete synthesis of the particle can expose the core surface antigens. These core antigens may be determined in the same fashion as the surface antigens. Core antigen may be prepared from intact particles by contacting the particles with a detergent such as sodium dodecyl sulfonate which ruptures the envelope by acting on its lipid content. The core may be readily separated from the residual disrupted envelope by conventional procedures such as ultracentrifugation or precipitation. The separated core or envelope antigens may be labelled as described below or used as immunogen to prepare antibodies.

Antibodies to either or both of surface or core antigen may be assayed. Such antibodies will generally fall into two diagnostically interesting classes, immune globulins G (IgG) and M (IgM). It is preferred to assay for IgM as it is the antibody class containing specificity for particle antigens which first appears during the course of infection, when IgG synthesis may not yet have been initiated. IgG assays may be material for regulatory purposes because this immune globulin fraction is detectable for many months after infection, thus demonstrating that a potential blood donor has at one time been exposed to the particle antigen even though the donor may no longer be infectious.

Methods for determining IgG or IgM of specific activity are conventional; any such method may be employed herein. For example, the IgG and IgM fractions of a test sample may first be separated by conventional procedures, most conveniently by specifically absorbing either fraction to an insoluble surface. For example, insoluble anti-IgG or anti-IgM antibodies of a first animal will bind the immune globulins of a second animal against which the first animal is immunized. DEAE or QAE-cellulose may be used to differentiate IgM from IgG. Boyle et al., ("J. Immunological Methods" 32 (1):51–8 [1980]) disclose that immobilized staphylococcal Protein A and concanavalin A will receive IgG or IgM antibodies, respectively. Thus, any of the foregoing specific adsorbents may be employed to separate IgG from IgM. Then the presence of anti-particle antigen specificity in either globulin fraction can be readily evaluated by measuring the binding of labelled particle antigen.

Either heterogeneous or homogeneous immunoassay techniques are satisfactory for determining particle antigens. It is preferred to use heterogeneous assays when determining intact particles or large antigenic fragments. All heterogeneous methods by definition include a step of separating antibody-bound antigen from residual antigen remaining in solution. In such methods the viral antibody is insolubilized before the assay, as for example by adsorption onto plastic beads or the inner wall of a plastic test tube, or by binding to anti-antibody already so adsorbed. The antibody may alternatively be insolubilized after the immune reaction with antigen has taken place, e.g., by precipitation with a second antibody. A representative heterogeneous assay is the "competitive" method. Here, an unlabelled sample antigen (if any) and labelled particle-antigen analogue compete for a limited number of particle antibody binding sites, the antibody-bound antigen is separated from the free antigen and the distribution of labelled antigen determined. This method is preferred for the assay of antibodies to the particle. In such a case, the antigen is insolubilized, and labelled and sample antibody compete for limited antigen sites.

The sandwich heterogeneous method is another technique which can be used. This method is preferred for the determination of particle antigen, particularly when found in intact particles or large fragments. The method comprises adsorbing the sample antigen onto insoluble antibody to particle antigen, removing the residual sample, adsorbing labelled particle antibody onto the antigen, removing excess labelled antibody and determining the distribution of label, usually by assaying the amount of label found in the solid phase. A variant of this method includes directly adsorbing antigen from the sample onto a nonspecific adsorbent, e.g., plastic, followed by labelled particle antibody or, sequentially, particle antibody and labelled antigen.

Another suitable technique is sequential saturation. As with the sandwich method, a surplus of insoluble antibody to particle antigen is used to bind the sample antigen, if any. However, rather than next contacting the insoluble antibody-antigen complex with labelled antibody, labelled antigen is added to occupy the remaining antibody sites. Excess labelled antigen is removed and the label content of one of the separated phases is determined.

Homogeneous immunoassay methods may also be employed to advantage. These methods have in common the elimination of the above-described phase separation; the complete determination can be conducted entirely with water soluble reagents. One such method comprises labelling an enzyme with particle antigen to form a conjugate, followed by admixing the conjugate, particle antibody and sample, and determining the change in enzyme activity brought on by binding of free antibody by the conjugate. Additional disclosure of this method may be found in U.S. Pat. No. 3,817,837, incorporated herein by reference.

Another homogeneous assay, which incidently may also be used in a heterogeneous mode, is disclosed in U.S. Pat. No. 3,935,074, also incorporated by reference. Here an antigen conjugate is formed by covalently linking the antigen with a detector ligand. Antibodies to the antigen and detector ligand are then mixed with the conjugate and sample. The usual practice is to then measure the residual unbound detector ligand antibody, which will be found in inverse relation to the amount of particle antigen.

Other suitable assay systems are disclosed in U.S. Pat. Nos. 4,006,360; 4,134,792 and 3,996,345; Yorde et al., "Clinical Chemistry" 22 (8): 1372-1377 (1976) and U.S. patent application Ser. No. 572,008, all of which are incorporated by reference. Additional methods will be apparent to those skilled in the art.

The labels to be used in some of the above methods may be dictated by the technology underlying the assay, as will be recognized by the skilled artisan. In most cases, however, the method is not dependent upon use of a particular label. Thus, any known label will be satisfactory, e.g., radioisotopes, enzymes, coenzymes, phages, stable free radicals, and fluorescent and luminescent substituents. Preferred labels are radioisotopes, particularly $^{125}I$, or enzymes.

The particle antigens or antibodies may be labelled with radioiodine in any conventional manner. Suitable methods use chloramine-T or lactoperoxidase, e.g., as disclosed by Dermody et al., "Clinical Chemistry" 25 (6): 989-995 (1979) or Parsons et al., "Analytical Biochemistry" 95:568-574 (1979), externally radioiodinated small molecules such as ($^{125}I$) iodohydroxyphenyl propionate-N-hydroxysuccinimate ester (Bolton et al., "Biochem. Journal" 133: 529-533 [1973]), ($^{125}I$) diiodofluorescein isothiocyanate (Gabel et al., "Analytical Biochemistry" 86:396-406 [1973]), tertiary-butyloxycarbonyl-L-($^{125}I$) iodotyrosine N-hydroxysuccinimide ester (Assoian et al., "Analytical Biochemistry 103:70-76 [1980]), or ICl (Montelaro et al., "Analytical Biochemistry" 99:92-96 [1979]). While the chloramine-T method is preferred for radiolabelling antibody or the particle core, the technique disclosed by Montelaro et. al. is preferred for labelling the particle envelope.

The invention will be more fully understood by reference to the following contemplated examples.

EXAMPLE 1

Urine procured from a hospitalized patient diagnosed to be in the acute phase of NANB hepatitis is preliminarily centrifuged at 8500 g for 10 min. 1 ml of the supernatant is layered in a 4 ml linear gradient of sucrose (10-20%), then ultracentrifuged for 3 hours at 240,000 g using an SW 50 rotor in a Beckman L5.65B centrifuge. The pellet is resuspended in 50 to 100 $\mu$l of 0.01 M tris saline buffer at pH 7.2. The specimen is applied to carbon grids, negatively stained with 1% uranyl acetate and examined in a Jeol 100 electronmicroscope. A serum sample from an acute phase haemodialysate patient is treated in the same manner. In both samples togavirus-like particles are observed having an outer diameter of 54-57 nm and a nucleocapsid of about 40 nm.

EXAMPLE 2

A urine sample in which the togavirus-like particles described in Example 1 had been visualized is centrifuged at 8500 g for 10 min. An equal volume of 28% polyethylene glycol (average molecular weight 6000) solution is added to the supernatant. The resulting precipitate is centrifuged at low speed until the suspension is clarified. The pellet is dissolved in tris buffer, sufficient ammonium sulfate added to produce a concentration of 15% of saturation, the resulting precipitate centrifuged until the suspension is clarified, the pellet dissolved in tris buffer and lyophilized or frozen for storage at $-70°$ C.

EXAMPLE 3

A urine sample containing the particles is purified by filtering the tris suspended pellet described in Example 1 through a Romicon filter membrane having an average pore diameter of 0.8 microns, followed by ultrafiltration with a Milipore PTHK membrane having a retention capability for molecules and particles of molecular weight greater than 100,000. The ultrafiltration is conducted at a slow rate so as to minimize damage to the particles by fluid shear at the membrane. After three volumes of tris buffer are passed through the retentate, thereby washing the particles free of lower molecular weight proteins, the retentate is ultrafiltered to one-tenth of the applied sample volume, the membrane briefly back-flushed with tris buffer, the retentate recovered and lyophilized or frozen at $-70°$ C.

EXAMPLE 4

The particle may be radioiodinated by the following method. The particles are suspended in phosphate buffered saline at pH 7.4. A stock solution of ICl is prepared by diluting 0.56 g KI, 0.33 mg NaIO$_3$, 29.2 g NaCl and 210 ml of concentrated HCl to 250 ml with distilled water. Immediately before use, this stock solution is extracted several times for 2 min. with 3 ml of chloroform until the chloroform is no longer colored pink. Residual chloroform is removed from the ICl stock by bubbling water saturated air for 5 min. Finally, 1 ml of ICl stock is thoroughly mixed with 10 ml of 2M NaCl. 0.1 ml of disrupted particle suspension is diluted with an equal volume of 1 M glycine buffer (pH 8.5) and mixed with 1 mCi of Na$^{125}$I in 0.1 m. glycine buffer. The iodination is started immediately by adding 0.1 ml of the final ICl preparation and allowed to proceed for 5–10 seconds. The product is rapidly separated from unreacted $^{125}$I by gel filtration through a column (0.9×15 cm) of Sephadex G-25 beads and eluted with phosphate buffered saline.

EXAMPLE 5

To a purified suspension of particles (1×10$^9$/ml) in phosphate buffered saline is added formaldehyde to a final concentration of 1:4000 and the mixture incubated with continuing agitation for 1 day at 37° C. and then 5 days at 40° C. The reaction mixture is partially neutralized with sodium bisulfite to leave a final concentration of 10 $\mu$/ml formaldehyde. This vaccine was stored at 4° C.

The inactivated particles are subcutaneously administered to chimpanzees with a protocol of three injections at one month interval and a booster one year later.

EXAMPLE 6

The culture medium of Morgan et al.. ("Proc. Soc. Exp. Biol. Med.", 73: 1 [1950]) is modified by adding 10% foal serum, 50 $\mu$g of dihydrostreptomycin/ml and 100 units of benzylpenicillin/ml. The medium is sterilized by filtration through a 0.22 micron filter. An aliquot of the medium is placed into a plastic Falcon flask, followed by an inoculum of WI38 human diploid cells. The inoculated medium is incubated at 37° C. until cellular confluence is achieved. A urine sample containing particles at a concentration of about 1×10$^7$ particles/ml is added to the medium in a volumetric proportion of 1:75. The culture is incubated at 37° C. while maintaining the pH at about 7.4 with dilute NaOH or HCl as appropriate. After about 7 days of incubation, cytotoxic effects on the tissue culture were noted, particularly conversion of the fibroblast cell line into substantially spherical, birefringent cells and, ultimately, cell lysis.

The product particles are harvested from the passage culture by decanting the supernatant from the cell culture flask, centrifuging at low speed to remove cell debris, precipitating the virus by adding polyethylene glycol 6000 to a concentration of about 15% and centrifuging. The virus pellet was resuspended in a composition consisting of one half part by volume of the culture medium without foal serum and one half part glycerol. The particles were stable in this composition when stored at −20° C.

EXAMPLE 7

Purified particle antigen in Freunds adjuvant is subcutaneously injected into rabbits on a biweekly basis for 14 weeks. The serum is harvested from the animals and the globulins precipitated with 15% ammonium sulfate. The precipitate is dissolved and dialyzed overnight in 200 volumes of 0.04 M phosphate buffer (pH 7.2). The solution is passed through a DEAE-cellulose column (1×20 cm) and the IgG fraction eluted with the same buffer. 50 $\mu$g alignots are radiolabeled with $^{125}$I following Greenwood et al., "Biochem. J." 89:114–123 (1963). The labelled IgG is separated from free radioiodine by passage through a column of Sephadex G-50. The labelled IgG is diluted to about 3 uCi/ml in a diluent of 50% calf serum, 5% human serum negative for antibody particle antigen and 0.1% NaN$_3$. This preparation is stored at 4° C.

EXAMPLE 8

1 ml of guinea pig serum obtained from animals immunized against the particles is coated onto the inner surface of a polypropylene test tube in accordance with U.S. Pat. No. 3,646,346. 0.1 ml of a urine specimen from an acute NANB hepatitis patient and 0.1 ml of a control specimen known to be free of the particles are then placed into coated tubes and incubated for 12 hours. The unbound elements of the sample are washed from each tube with water, radiolabelled antibody of Example 7 added to each tube and incubated for 12 hours, unbound labelled antibody washed from the tube with water and the radioactivity bound to the tube counted. The particle antigens gens could be satisfactorily detected by determining the extent of bound radioactivity in the assay tube compared to the control tube.

We claim:

1. A method, which comprises assaying a sample suspected to contain NANB hepatatis virus antigens for an antigen of at least one of togavirus strains ATCC VR-2011, VR-2012, VR-2013 or VR-2014.

2. A method, which comprises assaying a sample suspected to contain immune globulin to NANB hepatitis for immune globulins capable of binding an antigen of at least one of togavirus strains ATCC VR-2011, VR-2012, Vr-2013 or VR-2014.

3. The method of claim 2 wherein the immune globulin is IgM.

4. The method of claim 2 wherein the immune globulin is IgG.

5. An inmunoassay for determining NANB hepatitis infection in a patient, which comprises assaying a sample from said patient for IgM capable of binding an antigen of at least one of togavirus strains ATCC VR-2011, VR-2012, VR-2013 or VR-2014.

6. A method for recovering NANB hepatitis antigens, comprising separating from urine an antigen of at least one of togavirus strains ATCC VR-2011, VR-2012, VR-2013 or VR-2014.

7. A method for detecting NANB hepatitis, which comprises assaying for a particle antigen of at least one of togavirus strains ATCC VR-2011, VR-2012, VR-2013 or VR-2014 in urine.

8. A method for assaying a sample suspected to contain NANB hepatitis virus antigens which comprises detecting or determining in said sample an antigen of at least one of togavirus strains ATCC VR-2011, VR-2012, VR-2013 or VR-2014.

* * * * *